(12) United States Patent
Matsuo et al.

(10) Patent No.: US 8,317,684 B2
(45) Date of Patent: Nov. 27, 2012

(54) ENDOSCOPE AND ATTACHING METHOD OF CONNECTION MOUTH RING TO END OF ENDOSCOPIC FLEXIBLE TUBE

(75) Inventors: Shigeki Matsuo, Kokubunji (JP); Takatoshi Umeta, Hachioji (JP); Shigeru Kosuki, Hachioji (JP)

(73) Assignee: Olympus Medical Systems Corp. (JP)

( * ) Notice: Subject to any disclaimer, the term of this patent is extended or adjusted under 35 U.S.C. 154(b) by 1016 days.

(21) Appl. No.: 12/334,960

(22) Filed: Dec. 15, 2008

(65) Prior Publication Data

US 2009/0171158 A1 Jul. 2, 2009

(30) Foreign Application Priority Data

Dec. 26, 2007 (JP) ................. 2007-335326

(51) Int. Cl.
*A61B 1/00* (2006.01)

(52) U.S. Cl. ............. 600/140; 600/125; 600/139

(58) Field of Classification Search .......... 600/125, 600/139–140
See application file for complete search history.

(56) References Cited

U.S. PATENT DOCUMENTS

| | | | | |
|---|---|---|---|---|
| 3,948,251 A | * | 4/1976 | Hosono | 600/144 |
| 4,329,980 A | * | 5/1982 | Terada | 600/144 |
| 4,779,612 A | * | 10/1988 | Kishi | 600/141 |
| 4,807,598 A | * | 2/1989 | Hasegawa | 600/140 |
| 4,977,887 A | * | 12/1990 | Gouda | 600/144 |
| 5,275,152 A | * | 1/1994 | Krauter et al. | 600/129 |
| 5,465,710 A | * | 11/1995 | Miyagi et al. | 600/139 |
| 5,746,696 A | * | 5/1998 | Kondo | 600/139 |
| 6,083,152 A | * | 7/2000 | Strong | 600/139 |
| 6,485,411 B1 | * | 11/2002 | Konstorum et al. | 600/139 |
| 7,833,153 B2 | * | 11/2010 | Takeuchi et al. | 600/137 |

FOREIGN PATENT DOCUMENTS

JP 57-171311 10/1982

* cited by examiner

*Primary Examiner* — Matthew J Kasztejna
(74) *Attorney, Agent, or Firm* — Ostrolenk Faber LLP

(57) ABSTRACT

An endoscope includes a flexible tube having a helical tube in which a thin strip plate is helically wound, a braid tube covering the outside of the helical tube, and a flexible outer tube covering the outside of the braid tube, a connection mouth ring plastically deformed and fixed to an end of the flexible tube, and a helical tube displacement preventing portion which prevents displacement of the strip plate of the helical tube at the end of the flexible tube to which the connection mouth ring is fixed, when the connection mouth ring is fixed to the end of the flexible tube.

3 Claims, 12 Drawing Sheets

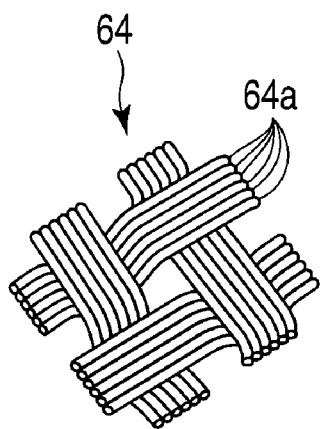
F I G. 3
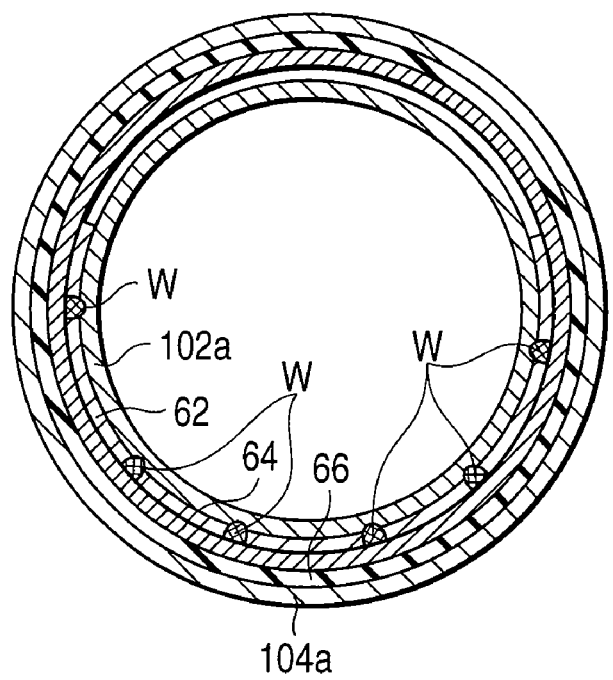
F I G. 4

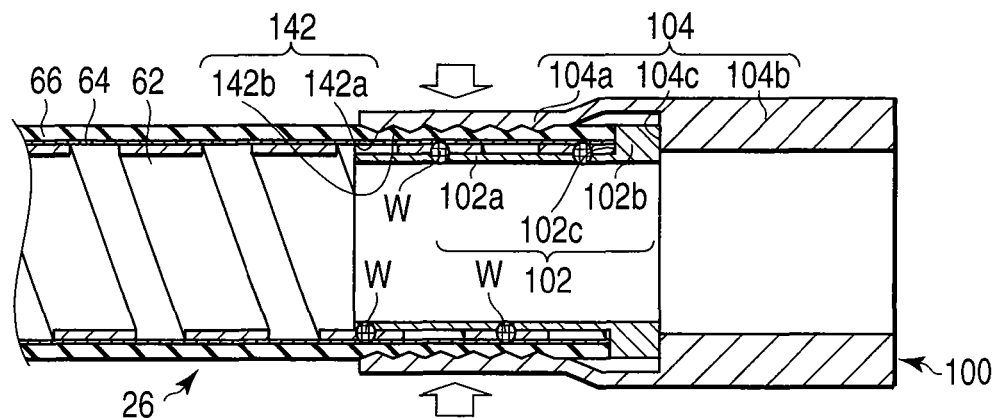
F I G. 8
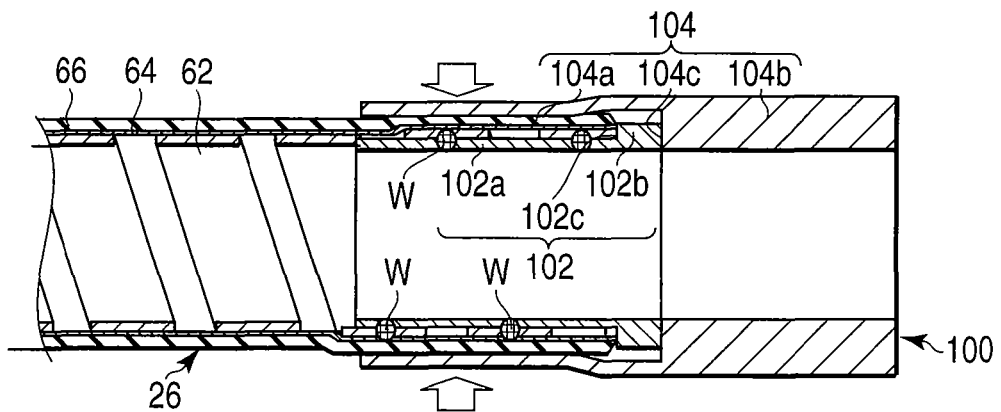
F I G. 9
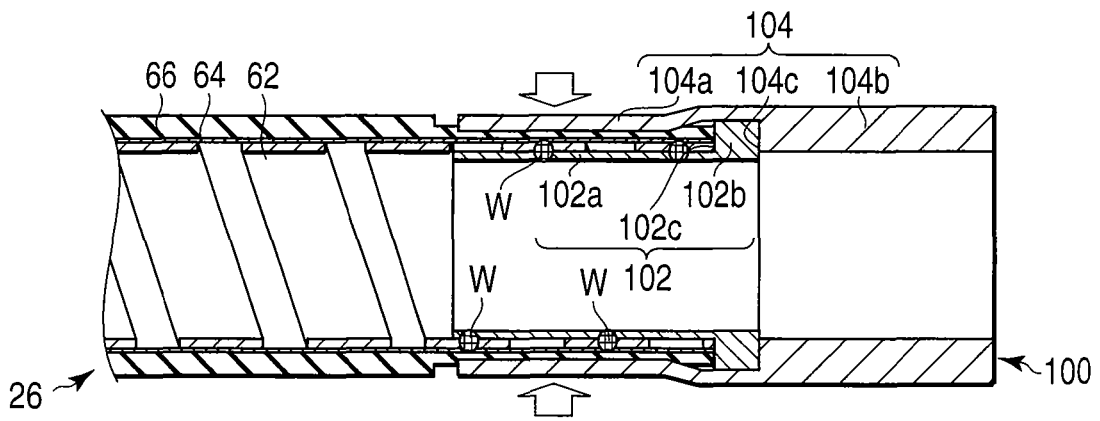
F I G. 10

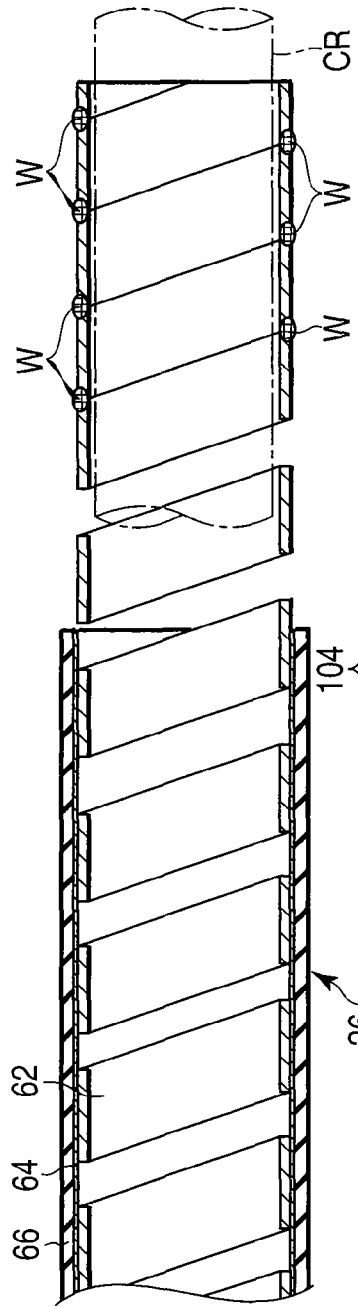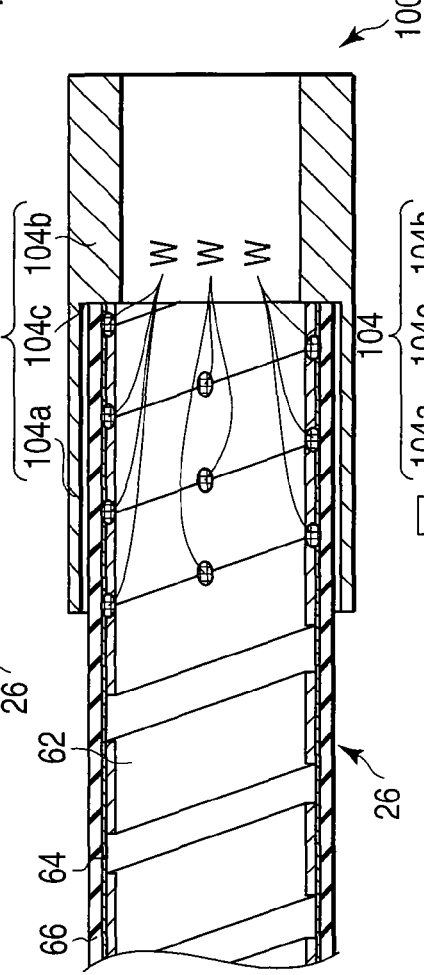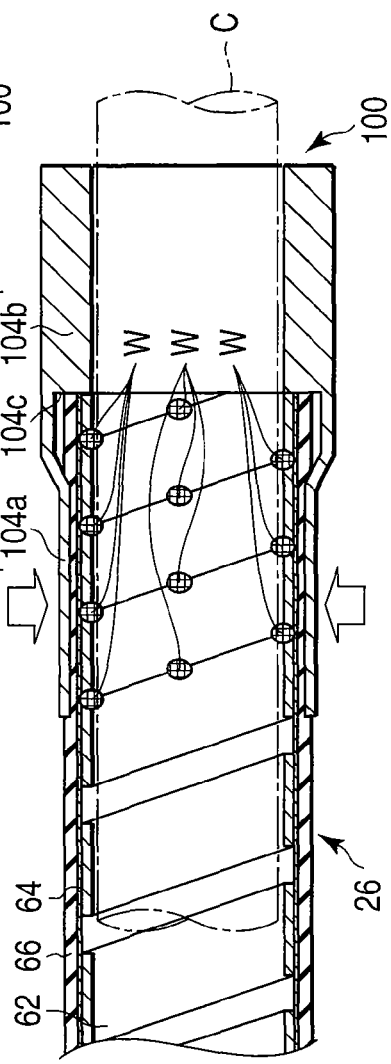

ENDOSCOPE AND ATTACHING METHOD OF CONNECTION MOUTH RING TO END OF ENDOSCOPIC FLEXIBLE TUBE

CROSS-REFERENCE TO RELATED APPLICATIONS

This application is based upon and claims the benefit of priority from prior Japanese Patent Application No. 2007-335326, filed Dec. 26, 2007, the entire contents of which are incorporated herein by reference.

BACKGROUND OF THE INVENTION

1. Field of the Invention

This invention relates to an endoscope which can be used for various purposes such as medical and industrial purposes, and an attaching method of connection mouth ring to an end of an endoscopic flexible tube.

2. Description of the Related Art

Heretofore, in manufacturing a flexible tube (flexible tube) used for an insertion portion or a universal cable of an endoscope, generally, a connection mouth ring has been fixed by adhesive bonding to a portion (hard portion) where a helical tube and a braid tube are braze-welded. However, braze welding requires a subsequent flux cleaning process, and the adhesive bonding requires time to complete the drying.

Thus, for example, Jpn. Pat. Appln. KOKAI Publication No. S57-171311 has disclosed a method of internally and externally clamping a braid tube between two connection mouth rings. This method can be applied to clamp all three layers forming a flexible tube which include a helical tube, a braid tube and a flexible outer tube between two connection mouth rings from the inside and outside of the flexible tube. If this method is used, the flexible tube can be cut at any part to attach the connection mouth ring in the final manufacturing process of the flexible tube, which permits a stable total length at completion.

In order to carry out such a method, a core bar is inserted through the inner connection mouth ring to prevent the diametrical reduction of the inner connection mouth ring, in which state the outer connection mouth ring is tightened (caulked) and plastically deformed.

BRIEF SUMMARY OF THE INVENTION

According to a first aspect of the invention, there is provided an endoscope including a flexible tube, a connection mouth ring, and a helical tube displacement preventing portion. The flexible tube includes a helical tube in which a thin strip plate is helically wound, a braid tube covering the outside of the helical tube, and a flexible outer tube covering the outside of the braid tube. The connection mouth ring is plastically deformed and fixed to an end of the flexible tube. The helical tube displacement preventing portion prevents displacement of the strip plate of the helical tube at the end of the flexible tube to which the connection mouth ring is fixed, when the connection mouth ring is fixed to the end of the flexible tube.

According to a second aspect of the invention, there is provided an attaching method of a connection mouth ring to an end of an endoscopic flexible tube. The flexible tube includes a helical tube in which a thin elastic strip plate is helically wound in a spaced manner, a braid tube covering the outside of the helical tube, and an outer tube covering the outside of the braid tube. The method includes: preventing displacement of the strip plate of the helical tube with regard to a predetermined region of an end of the helical tube; covering the outside of the predetermined region of the end of the helical tube with the connection mouth ring holding the braid tube and outer tube; disposing a core bar inside the predetermined region of the helical tube; plastically deforming and fixing the connection mouth ring from the outside of the flexible tube including the predetermined region of the helical tube; and smoothly removing the core bar from the inside of the predetermined region of the helical tube, by preventing displacement of the strip plate of the helical tube.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3 is a schematic perspective view showing part of a braid used for the insertion portion or a universal cable of the endoscope according to first to twelfth embodiments;

FIG. 4 is a schematic cross sectional view of the insertion portion along the line IV-IV in FIG. 2;

FIG. 8 is a schematic longitudinal sectional view showing how the operation portion connection mouth ring is fixed to the proximal end of the flexible tube of the insertion portion of the endoscope according to the third embodiment;

FIG. 9 is a schematic longitudinal sectional view showing how the operation portion connection mouth ring is fixed to the proximal end of the flexible tube of the insertion portion of the endoscope according to the fourth embodiment;

FIG. 10 is a schematic longitudinal sectional view showing how the operation portion connection mouth ring is fixed to the proximal end of the flexible tube of the insertion portion of the endoscope according to the fifth embodiment;

FIGS. 15A to 15C are schematic longitudinal sectional views of the insertion portion, sequentially continuing from FIG. 6B and showing the procedure of connecting the flexible tube of the insertion portion of the endoscope to the operation portion connection mouth ring according to the ninth embodiment;

DETAILED DESCRIPTION OF THE INVENTION

Hereinafter, embodiments of the present invention will be described with reference to the drawings. Although a medical endoscope is described by way of example in the following embodiments, the present invention is applicable not exclusively to the medical field, and also applies to other fields, such as industry.

First Embodiment

A first embodiment is described with reference to FIG. 1 to FIG. 6F.

Figure 1:
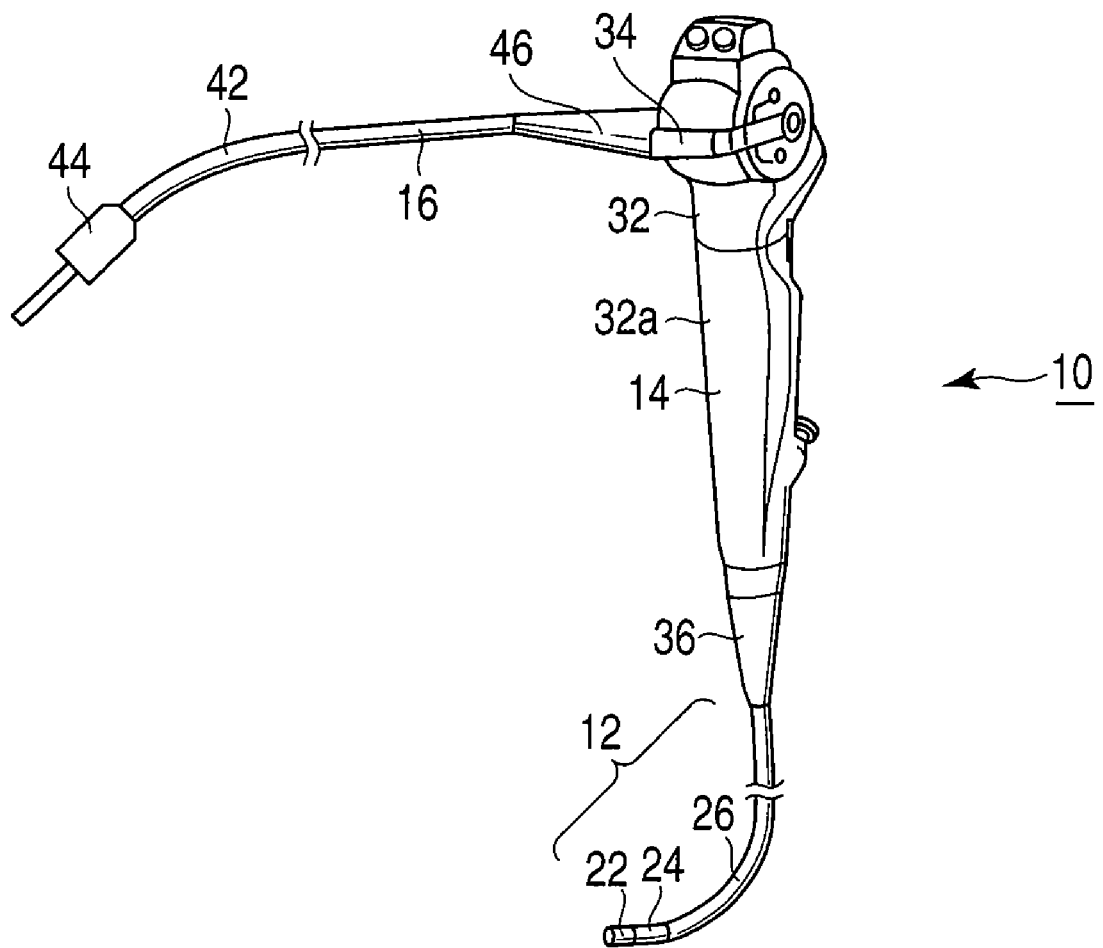
FIG. 1 is a schematic view showing an endoscope according to first to twelfth embodiments.

As shown in FIG. 1, an endoscope 10 includes an insertion portion 12 to be inserted into a narrow and small space, an operation portion 14 disposed at the proximal end of the insertion portion 12, and a universal cable 16 extending from the operation portion 14.

The insertion portion 12 includes a distal hard portion 22, a bending portion 24 disposed at the proximal end of the distal hard portion 22, and a flexible tube (corrugated tube) 26 disposed at the proximal end of the bending portion 24. The operation portion 14 includes an operation portion main body 32 with a grip portion 32a, a bending operation knob 34 disposed in the operation portion main body 32, and a protection hood 36 disposed at the proximal end of the flexible tube 26 and disposed in the grip portion 32a of the operation portion main body 32. The universal cable 16 includes a flexible tube 42 extending from the operation portion main body 32, a connector 44 disposed at the end of the flexible tube 42 on the distal side with respect to the operation portion main body 32, and an protection hood 46 disposed at the end of the flexible tube 42 on the proximal side with respect to the operation portion main body 32.

Figure 2:
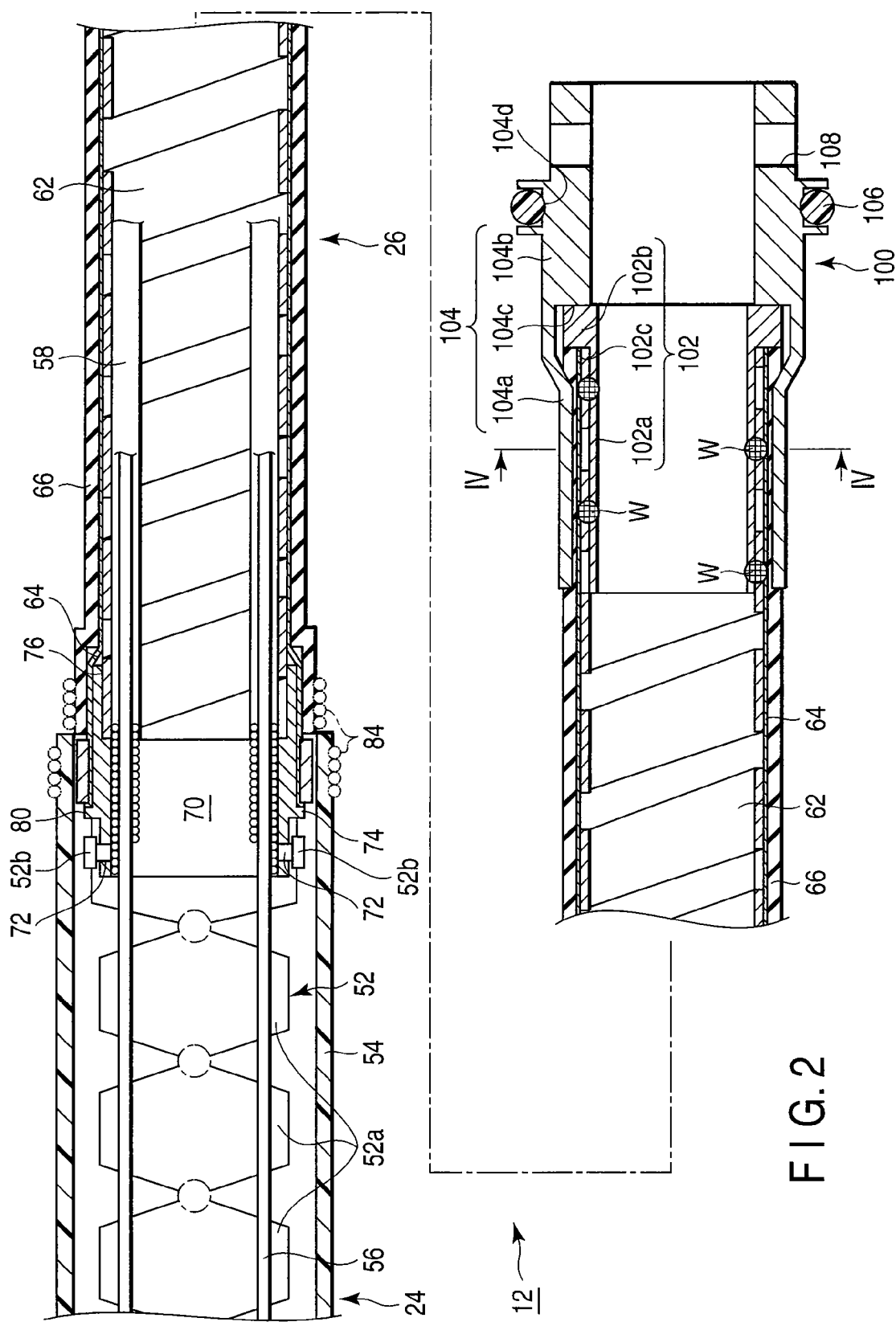
FIG. 2 is a schematic longitudinal sectional view showing a bending portion, a flexible tube, a connection mouth ring connecting the bending portion and the flexible tube of an insertion portion of the endoscope, and an operation portion connection mouth ring disposed at the proximal end of the flexible tube of the endoscope according to the first embodiment.

As shown in FIG. 2, the bending portion 24 of the insertion portion 12 includes a bending tube 52 which is bent by the operation of the operation portion 14, and a cover tube (outer tube) 54 disposed outside the bending tube 52. The bending tube 52 is formed by joining a plurality of bending pieces 52a so that they axially rotate with respect to each other. For example, a pair of operation wires 56 are inserted into each of the bending pieces 52a. These operation wires 56 have their proximal ends fixed to the bending operation knob 34 of the operation portion 14, and their distal ends fixed to the most distal bending piece 52a of the bending tube 52 or to the distal hard portion 22. That is, the operation wires 56 are inserted in the bending portion 24 and the flexible tube 26 of the insertion portion 12.

In addition, each of the operation wires 56 is covered with a cover coil 58. The distal ends of the cover coils 58 are fixed to the inner peripheral surface of a first connection mouth ring 70 described later by, for example, adhesive bonding or braze-welding (brazing or soldering). These cover coils 58 are disposed to extend up to the proximal side of the flexible tube 26. The proximal ends of the cover coils 58 may be fixed to a second connection mouth ring 100, described later, or may be what is called free ends.

The flexible tube 26 includes a helical tube 62, a braid tube 64 disposed outside the helical tube 62, and a flexible outer tube 66 disposed outside the braid tube 64.

The helical tube 62 is formed by helically winding a thin strip plate made of, for example, stainless steel into the shape of a substantially circular tube. The strip plate of the helical tube 62 is, for example, about 3 mm in breadth. The distal end of the helical tube 62 is cut so that it is about 90 degrees (including 90 degrees) to the longitudinal central axis of the helical tube 62.

As shown in FIG. 3, in the braid tube 64, bundles of a plurality of woven strands 64a made of, for example, stainless steel are formed into the shape of a substantially circular tube. The outer tube 66 is formed of a flexible resin material such as a rubber material into the shape of a substantially circular tube so that it covers the outside of the braid tube 64.

The proximal end of the bending tube 52 of the bending portion 24 is connected to the distal end of the flexible tube 26 via the first connection mouth ring (bending portion connection mouth ring) 70.

As shown in FIG. 2, the first connection mouth ring 70 is formed of, for example, a metal material such as stainless steel into a substantially cylindrical shape. At the distal end of the first connection mouth ring 70, for example, a pair of opposite openings 72 are formed so that connecting pins (or connecting screws) 52b for connecting the most proximal bending piece 52a of the bending tube 52 penetrates and is thus disposed in the openings. A diametrically outwardly projecting flange portion 74 is formed on the proximal side of the part of the first connection mouth ring 70 where the openings 72 are formed. Further, on the inner peripheral surface of the proximal end of the first connection mouth ring 70, there is formed a concave portion 76 having an inside diameter formed to be larger than the distal end of the first connection mouth ring 70.

The inner peripheral surface of the first connection mouth ring 70 forms one surface from its distal end to the distal end of the concave portion 76. The concave portion 76 of the first connection mouth ring 70 is formed to have an inside diameter larger than the inside diameter from the distal end of the first connection mouth ring 70 to the distal end of the concave portion 76. The outer peripheral surface of the first connection mouth ring 70 is formed so that the thickness from its distal end to the flange portion 74 is smaller than the thickness of the outer peripheral surface from the flange portion 74 to the position where the concave portion 76 is formed. Moreover, the outer peripheral surface of the first connection mouth ring 70 forms one surface from the flange portion 74 to the proximal end. That is, the first connection mouth ring 70 is formed to have the largest thickness at the position from the flange portion 74 to the distal end of the concave portion 76 in the axial direction of the first connection mouth ring 70.

The thickness of the first connection mouth ring 70 from its distal end to the flange portion 74 is suitably formed to consider the size of the head of the connecting pin 52b disposed in the pair of openings 72 from the outside of the first connection mouth ring 70. Specifically, the tops of the heads of the connecting pins 52b disposed in the openings 72 of the first connection mouth ring 70 are suitably positioned as high as or lower than the top of the flange portion 74.

The inside diameter of the concave portion 76 of the first connection mouth ring 70 is formed to be equal to or smaller than the outside diameter of the helical tube 62 so that the outer peripheral surface of the helical tube 62 may be in close contact with the inner peripheral surface of the concave portion 76 when the single helical tube 62 is placed in a natural state (state of no external force applied). The distal end of the helical tube 62 is cut at about 90 degrees to its axial direction. Thus, the outer peripheral surface of the helical tube 62 is urged against the inner peripheral surface of the concave portion 76 of the first connection mouth ring 70, and at the same time, the distal end of the helical tube 62 is in contact with a step portion of the distal end of the concave portion 76. That is, the distal end of the helical tube 62 is fitted in a positioned state in the concave portion 76 of the first connection mouth ring 70.

As shown in FIG. 2, while the first connection mouth ring 70 and the helical tube 62 are in a fitted state as described above, only the parts (with a width of, for example, about 1 mm in the axial direction) where the first connection mouth ring 70 and the helical tube 62 overlap are spot-welded by laser from the outside of the first connection mouth ring 70 at proper intervals or continuously, such that welded portions welded at predetermined intervals or welded in a continuous circumferential (arc-like) shape are formed. That is, the welded portions are formed in the first connection mouth ring 70 circumferentially or along the helical of the helical tube 62. At this point, the first connection mouth ring 70 is instantaneously heated in the laser welding, so that the transmission of heat from the first connection mouth ring 70 to the outer tube 66 is prevented to the maximum even if the welding takes place in the vicinity of the outer tube 66.

Furthermore, the distal end of the braid tube 64 is disposed on the proximal side of the flange portion 74 of the first connection mouth ring 70 and outside the first connection mouth ring 70. A caulking member 80 is disposed outside the braid tube 64. The caulking member 80 is formed of, for example, a metal material such as stainless steel so that its axial width is about 2 mm. It is also suitable for the caulking member 80 to be, for example, ring shaped or C-shaped.

The caulking member 80 is positioned substantially in contact with the flange portion 74 of the first connection mouth ring 70. That is, the flange portion 74 of the first connection mouth ring 70 functions as a positioning member of the caulking member 80. Here, while the axial length of the caulking member 80 can be properly set, it is suitable for the proximal end of the caulking member 80 to be at the same position as the outer periphery of the distal end of the concave portion 76 of the first connection mouth ring 70 or to be at a position closer to the distal side. Therefore, if the caulking member 80 is about 2 mm, as described above, the length of the first connection mouth ring 70 between the proximal end surface of the flange portion 74 and the distal end of the concave portion 76 has only to be formed to be slightly larger. When the caulking member 80 is caulked (plastically deformed) with respect to the outside of the first connection mouth ring 70, the caulking member 80 is positioned with respect to the first connection mouth ring 70 by the flange portion 74, and the braid tube 64 is held and fixed between the outside of the first connection mouth ring 70 and the inside of the caulking member 80.

While the bending tube 52 of the bending portion 24 and the flexible tube 26 are thus fixed to the first connection mouth ring 70, the cover tube 54 of the bending portion 24 covers from the outside. The proximal end of the cover tube 54 is wound with a thread 84 from the outside of the cover tube 54 so that the caulking member 80 is pressed in a diametrically inward direction of the first connection mouth ring 70. The thread 84 is wound, without space, not only around the proximal end of the cover tube 54 of the bending portion 24 but also around the distal end of the outer tube 66 of the flexible tube 26. An unshown adhesive is applied to the thread 84 to provide watertightness between the proximal end of the cover tube 54 of the bending portion 24, the distal end of the outer tube 66 of the flexible tube 26 and the first connection mouth ring 70. At this point, the caulking member 80 is disposed inside the cover tube 54 and can therefore be insulated from the outside of the insertion portion 12. The caulking member 80 and the first connection mouth ring 70 are disposed in a layer under the part which is wound with the thread 84 and to which the adhesive is applied, so that this part (the layer under the part to which the adhesive is applied) is not bent. Thus, the adhesively bonded part in which the adhesive is applied to the thread 84 is prevented from cracking.

Subsequently, a structure is described with reference to FIG. 2 and FIG. 4 whereby the second connection mouth ring (operation portion connection mouth ring) 100 for connecting to the operation portion 14 is connected to the flexible tube 26 of the insertion portion 12 of the endoscope 10.

As shown in FIG. 2 and FIG. 4, the second connection mouth ring 100 includes an inner mouth ring 102 and an outer mouth ring 104 that are substantially cylindrical. The inner mouth ring 102 and the outer mouth ring 104 are formed by, for example, a metal material such as stainless steel.

The inner mouth ring 102 includes a cylindrical portion 102a disposed inside the helical tube 62, and an outward flange portion 102b disposed at the proximal end of the cylindrical portion 102a. The cylindrical portion 102a and the outward flange portion 102b have the same inside diameter and are flush with each other. Further, the outward flange portion 102b projects diametrically outwardly with respect to the outer peripheral surface of the cylindrical portion 102a. Thus, a step portion (collision portion) 102c is formed between the cylindrical portion 102a and the flange portion 102b. The proximal ends of the helical tube 62, the braid tube 64 and the outer tube 66, that is, the proximal end of the flexible tube 26 are positioned by the step portion 102c.

The outside diameter of the inner mouth ring 102 is formed to be larger than the inside diameter of the proximal end of the helical tube 62 so that the inner peripheral surface of the helical tube 62 may be in close contact with the outer peripheral surface of the inner mouth ring 102 when the helical tube 62 is placed in a natural state. The helical tube 62 is fixed to the inner mouth ring 102 by being spot-welded by, for example, a laser from the outside of the helical tube 62. That is, as shown in FIG. 4, welded portions (helical tube displacement preventing portions) W are formed. Thus, when a later-described cylindrical portion 104a of the outer mouth ring 104 is caulked (plastically deformed), the helical tube 62 is prevented from being moved (displaced), for example, in the longitudinal direction of the cylindrical portion 102a of the inner mouth ring 102 and the helical direction of the strip plate of the helical tube 62. That is, the pitch of the helical tube 62 is maintained. This prevents the helical tube 62 from tightening the cylindrical portion 102a of the inner mouth ring 102 and reducing the inside diameter of the cylindrical portion 102a of the inner mouth ring 102.

In addition, it is possible to visibly recognize the part where the helical tube 62 and the inner mouth ring 102 overlap from the outside of the inner mouth ring 102. This enables the helical tube 62 and the inner mouth ring 102 to be more securely fixed by laser welding.

The outer mouth ring 104 includes the cylindrical portion 104a disposed outside the flexible tube 26, and an inward flange portion 104b disposed at the proximal end of the cylindrical portion 104a. The cylindrical portion 104a and the inward flange portion 104b have the same inside diameter and are flush with each other. The inward flange portion 104b projects diametrically inwardly with respect to the outer peripheral surface of the cylindrical portion 104a. Thus, a step portion (collision portion) 104c is formed between the cylindrical portion 104a and the flange portion 104b. The outside diameter of the flange portion 102b of the inner mouth ring 102 is smaller than the inside diameter of the cylindrical portion 104a of the outer mouth ring 104, and larger than the inside diameter of the inward flange portion 104b. Moreover, the proximal end of the inner mouth ring 102 is positioned by the step portion 104c between the cylindrical portion 104a and the flange portion 104b of the outer mouth ring 104.

The cylindrical portion 104a of the outer mouth ring 104 has such an inside diameter that not only the inner mouth ring 102 but also the helical tube 62, the braid tube 64 and the outer tube 66 are disposed therein.

A circular-ring-shaped groove 104d is formed in the outer peripheral surface of the inward flange portion 104b of the outer mouth ring 104. An O-ring 106 is disposed in the groove 104d. Further, for example, a pair of screw holes 108 are formed on the proximal side of the groove 104d.

Figure 5:
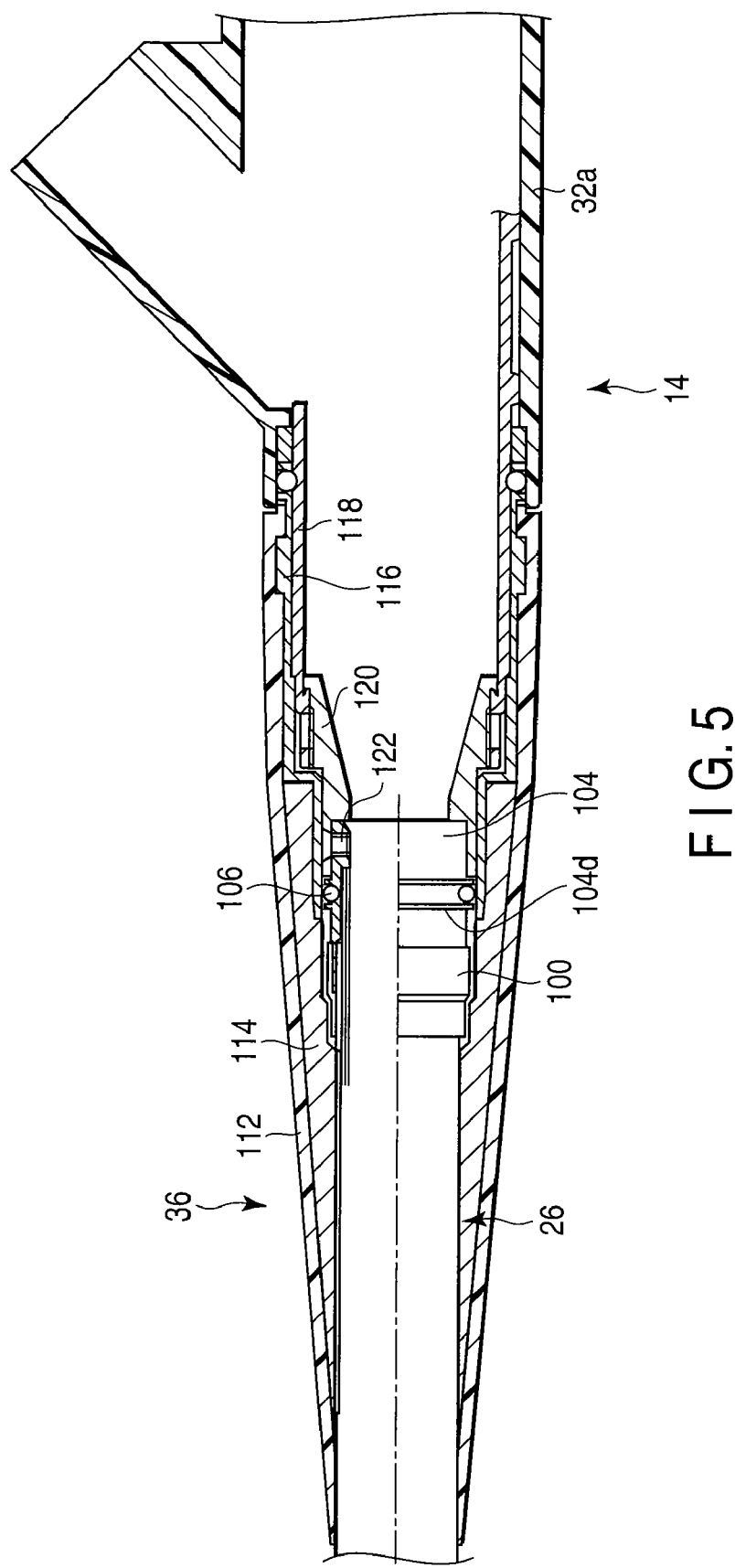
FIG. 5 is a schematic longitudinal sectional view of part of the insertion portion and an operation portion, showing how the operation portion connection mouth ring at the proximal end of the flexible tube of the insertion portion shown in FIG. 2 is disposed in a protection hood of the operation portion.

As shown in FIG. 5, the second connection mouth ring 100 disposed at the proximal end of the flexible tube 26 is fixed within the protection hood 36 of the operation portion 14.

The protection hood 36 includes an exterior portion 112, an interior portion 114, and first to third linkage members 116, 118, 120.

The exterior portion 112 is disposed on the outermost side of the protection hood 36. The interior portion 114 is disposed inside the exterior portion 112, and holds the proximal end of the flexible tube 26. The first linkage member 116 is fitted into the exterior portion 112 and the interior portion 114. The second linkage member 118 is screwed to the first linkage member 116, and, although not shown, is also linked to the grip portion 32a. Further, the third linkage member 120 is linked to the second linkage member 118, and is linked by disposing screws 122 in the screw holes 108 of the outer mouth ring 104 of the second connection mouth ring 100.

Next, a method of attaching the second connection mouth ring 100 to the proximal end of the flexible tube 26 is illustrated.

Figure 6A:
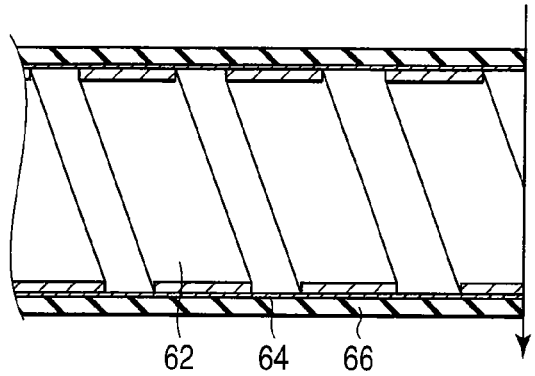
FIGS. 6A to 6F are schematic longitudinal sectional views of the insertion portion, sequentially showing the procedure of connecting the flexible tube of the insertion portion of the endoscope to the operation portion connection mouth ring according to the first embodiment.

First, as shown in FIG. 6A, the proximal ends of the helical tube 62, the braid tube 64 and the outer tube 66 are cut. At this point, the proximal ends of the helical tube 62, the braid tube 64 and the outer tube 66 are cut at about 90 degrees to their axial direction. Then, burrs in the proximal ends of the helical tube 62, the braid tube 64 and the outer tube 66 are removed so that the proximal end surface of the flexible tube 26 may be even.

Figure 6B:
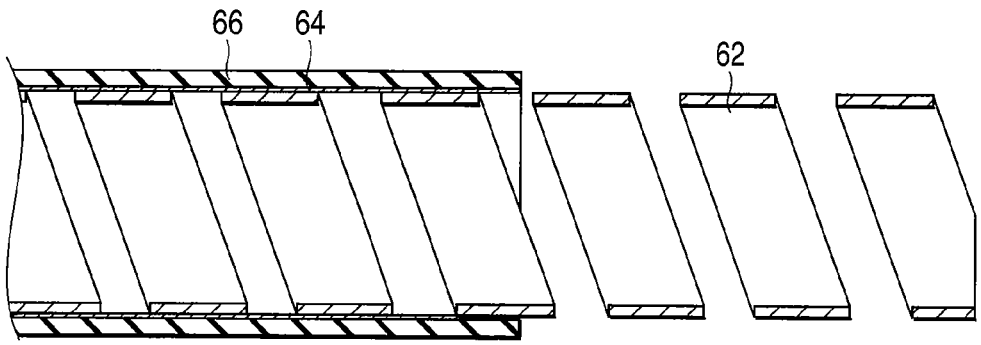

Then, as shown in FIG. 6B, the proximal end of the helical tube 62, of the helical tube 62, the braid tube 64 and the outer tube 66, is drawn to the proximal side with respect to the proximal ends of the braid tube 64 and the outer tube 66.

Figure 6C:
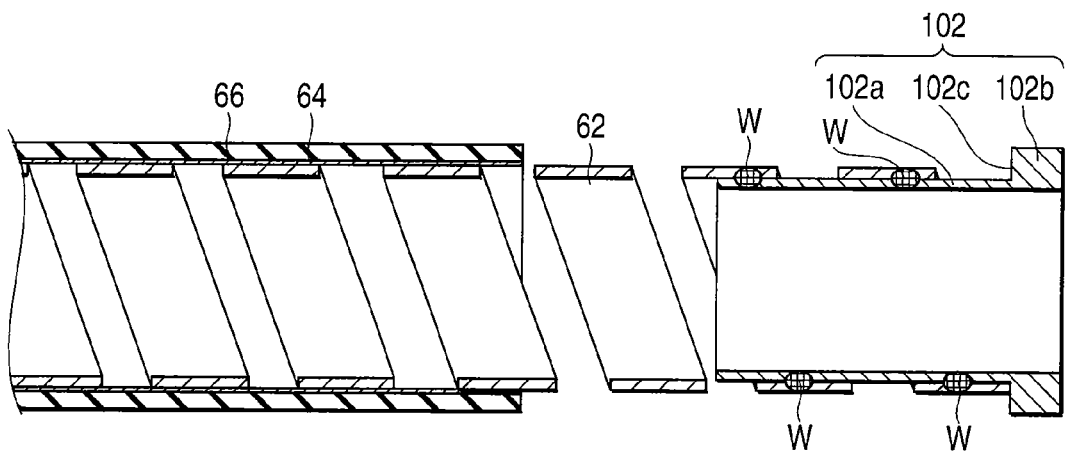

As shown in FIG. 6C, the inner peripheral surface of the helical tube 62 is disposed outside the cylindrical portion 102a of the inner mouth ring 102 of the second connection mouth ring 100, and the proximal end of the helical tube 62 is brought into contact with the step portion 102c. At this point, since the diameter of the inner peripheral surface of the helical tube 62 in a natural state is smaller than the outside diameter of the cylindrical portion 102a of the inner mouth ring 102, the inner peripheral surface of the helical tube 62 comes into close contact with the outer peripheral surface of the cylindrical portion 102a of the inner mouth ring 102. In this state, welding is carried out by applying a laser from the outside of the helical tube 62. At this point, the welding is carried out in an arc-shaped or spotted manner. Thus, the inner mouth ring 102 of the second connection mouth ring 100 is fixed to the proximal end of the helical tube 62. At this point, the end of the helical tube 62 collides with the step portion (collision portion) 102c of the inner mouth ring 102, so that the helical tube 62 can be axially positioned with respect to the inner mouth ring 102 of the second connection mouth ring 100.

Figure 6D:
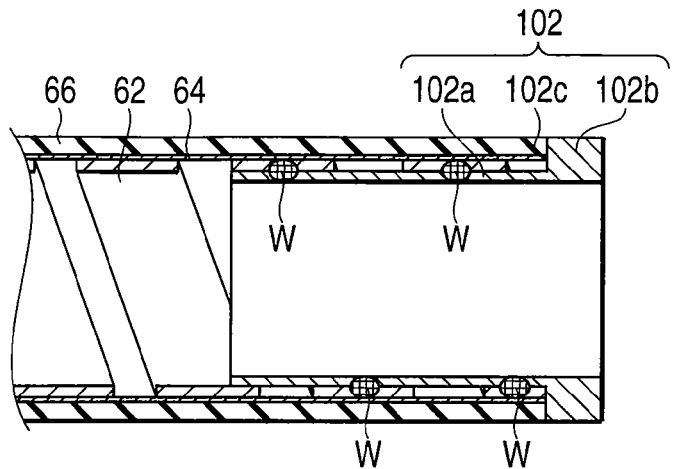

As shown in FIG. 6D, the inner mouth ring 102 of the second connection mouth ring 100 is fixed to the proximal end of the helical tube 62, in which condition the helical tube 62 is pressed into the braid tube 64. Then, the proximal end of the braid tube 64 and the proximal end of the outer tube 66 are brought into contact with the flange portion 102b of the inner mouth ring 102.

Figure 6E:
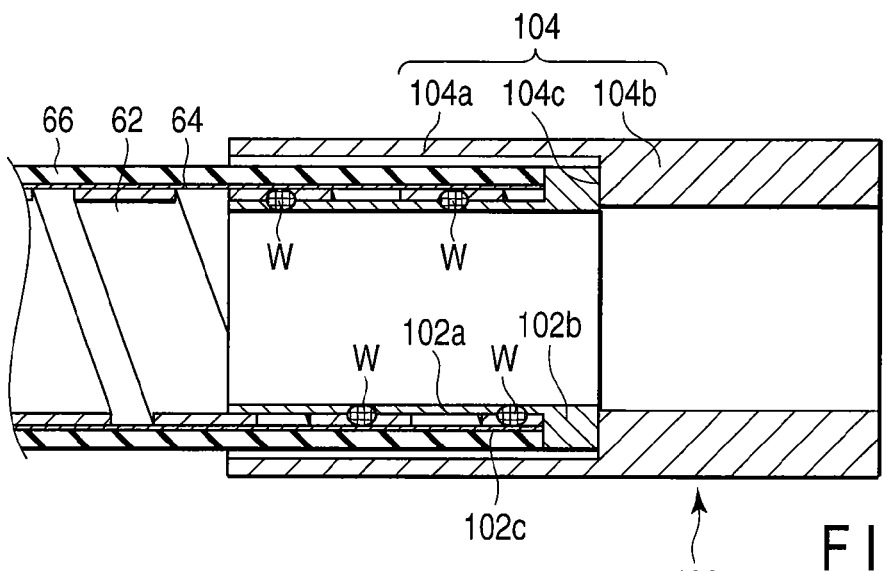

As shown in FIG. 6E, the cylindrical portion 104a of the outer mouth ring 104 is disposed outside the inner mouth ring 102, and the inward flange portion 104b of the outer mouth ring 104 is brought into contact with the proximal end of the outward flange portion 102b of the inner mouth ring 102.

Figure 6F:
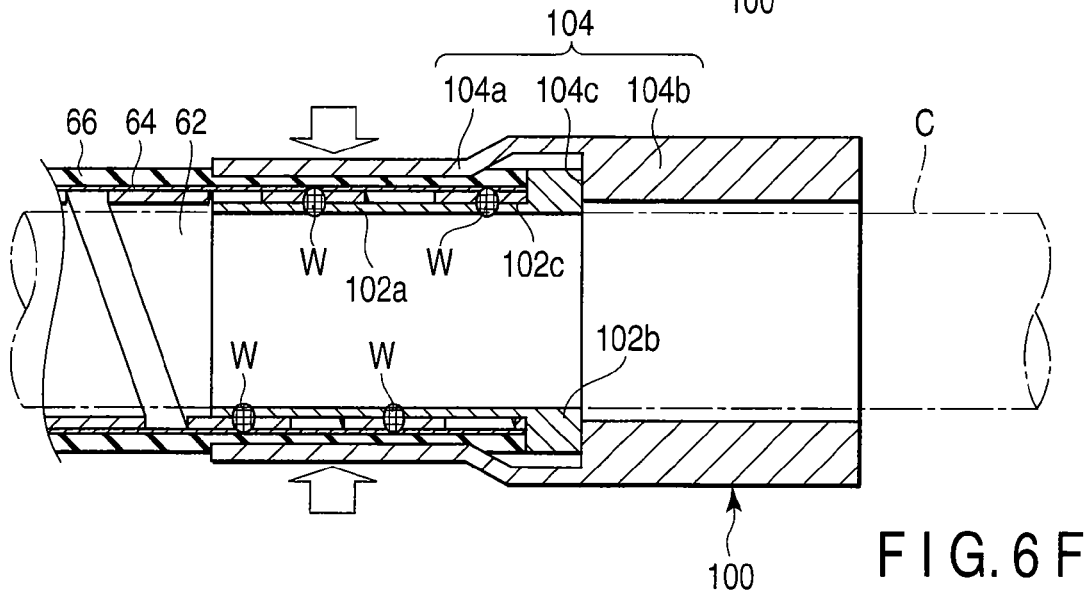

As shown in FIG. 6F, a core bar (caulking jig) C is put into the inner mouth ring 102. In this state, the cylindrical portion 104a of the outer mouth ring 104 is caulked (plastically deformed) inward. That is, the proximal ends of the helical tube 62, the braid tube 64 and the outer tube 66 are held and fixed between the inner peripheral surface of the cylindrical portion 104a of the outer mouth ring 104 and the outer peripheral surface of the cylindrical portion 102a of the inner mouth ring 102. When the cylindrical portion 104a of the outer mouth ring 104 is caulked inward, the inner peripheral surface of the inner mouth ring 102 is received by the core bar C to prevent the reduction of the inside diameter of the inner mouth ring 102. The proximal end of the helical tube 62 is fixed to the outside of the cylindrical portion 102a of the inner mouth ring 102, and the proximal end of the helical tube 62 is in collision with the step portion 102c of the inner mouth ring 102, so that even if the cylindrical portion 104a of the outer mouth ring 104 is strongly caulked and plastically deformed, tightening of the helical tube 62 is inhibited. This prevents the core bar C from being unable to be removed after the second connection mouth ring 100 is caulked at the proximal end of the flexible tube 26. Thus, it is possible to obtain a strength sufficient to fix the flexible tube 26 and the second connection mouth ring 100.

As described above, the following can be said according to this embodiment.

The proximal end of the flexible tube 26 is connected to the second connection mouth ring 100 in a condition where the helical tube 62 of the flexible tube 26 is fixed to the outside of the cylindrical portion 102a of the inner mouth ring 102 of the second connection mouth ring 100. This prevents the helical tube 62 from being moved (displaced) when the cylindrical portion 104a of the outer mouth ring 104 of the second connection mouth ring 100 is caulked at the proximal end of the flexible tube 26. Consequently, tightening of the helical tube 62 is inhibited, so that the flexible tube 26 can be firmly held (caulked) between the inner mouth ring 102 and the outer mouth ring 104 in such a manner as to inhibit the deformation of the inner mouth ring 102. Thus, tightening of the helical tube 62 is prevented to inhibit the deformation of the inner mouth ring 102, such that the core bar C can be easily removed after the second connection mouth ring 100 is fixed to the flexible tube 26.

In order to fix the second connection mouth ring 100 to the proximal end of the flexible tube 26, the helical tube 62 is fixed to the inner mouth ring 102, in which state the braid tube 64, the outer tube 66 and the outer mouth ring 104 have then only to be disposed outside the helical tube 62 to caulk the outer mouth ring 104. Therefore, the process of attaching the second connection mouth ring 100 to the flexible tube 26 can be carried out simply and in a short time with no need for the curing time of, for example, an adhesive.

In addition, in the case described in this embodiment, laser spot welding is used to fix the helical tube 62 to the inner mouth ring 102. However, if the helical tube 62 can be securely fixed to the inner mouth ring 102 more simply and in a shorter time, laser spot welding is not the exclusive means, and various other means (adhesive bonding and other thermal method by, e.g., welding) can be used.

While the second connection mouth ring 100 is provided as a connection mouth ring for connecting the flexible tube 26 to the operation portion 14 in the above description, it is also suitable to use the second connection mouth ring 100 to connect the flexible tube 42 and the connector 44 of the universal cable 16 or to connect the flexible tube 42 of the universal cable 16 and the operation portion 14.

In the example (the example in which the bending portion 24 curves in two directions) described in this embodiment, the pair of operation wires 56 are disposed inside the bending tube 52 for the simplification of the drawings and explanation, as shown in FIG. 2. Although not shown, it is also suitable, for example, to dispose the pair of operation wires inside the bending tube 52. In such a structure, the bending portion 24 can curve in four directions.

Second Embodiment

Next, a second embodiment is described with reference to FIG. 7. This embodiment is a modification of the first embodiment, and the same symbols are assigned to the same members as the members described in the first embodiment or the members having the same effects, and such members are not described in detail. This holds true with the third to twelfth embodiments.

Figure 7:
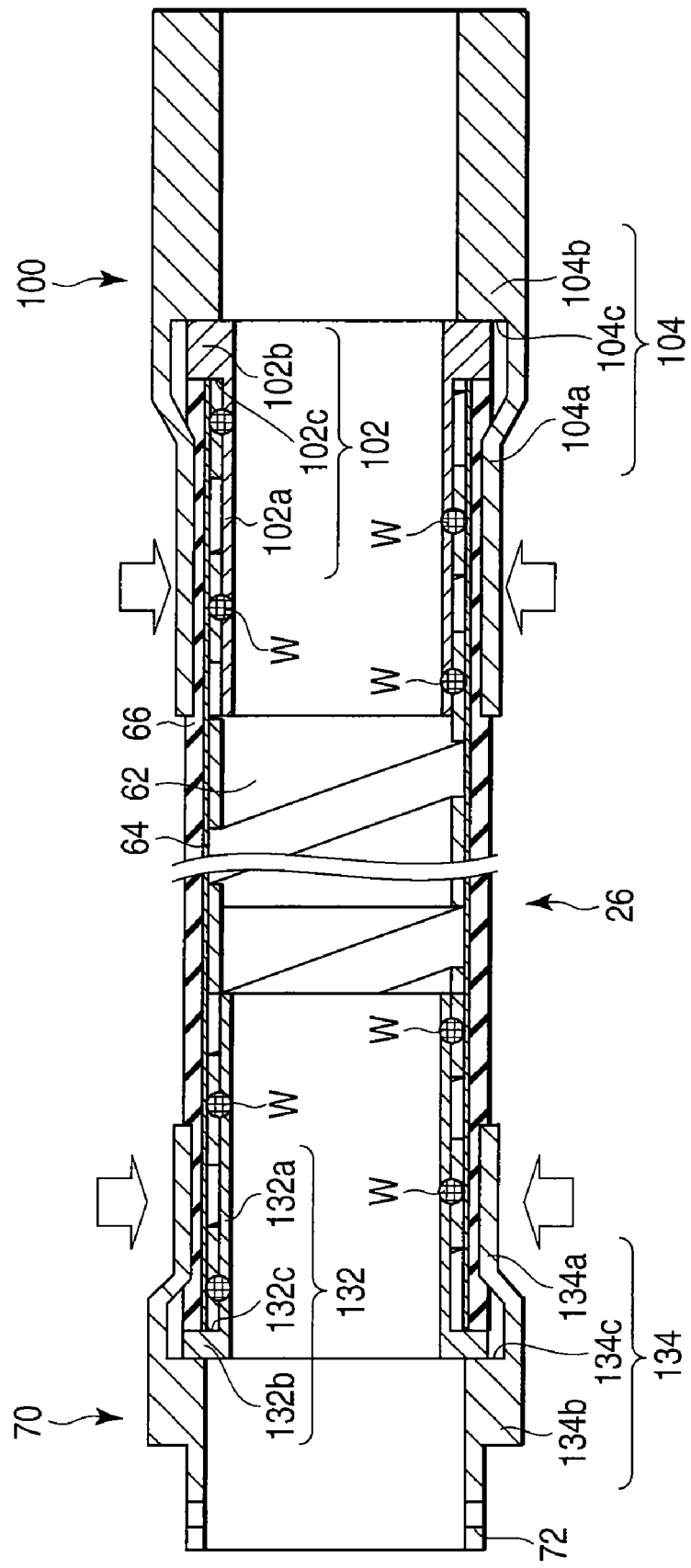
FIG. 7 is a schematic longitudinal sectional view showing how a connection mouth ring is fixed to the distal end of the flexible tube of the insertion portion of the endoscope by the same structure as the structure described in the first embodiment for fixing the operation portion connection mouth ring to the proximal end of the flexible tube, and the operation portion connection mouth ring described in the first embodiment shown in FIG. 2 is fixed to the proximal end of the flexible tube according to the second embodiment.

In the example of this embodiment, the structure used to fix the second connection mouth ring 100 to the proximal end of the flexible tube 26 shown in FIG. 2 in the first embodiment is used to fix a first connection mouth ring 70 to the distal end of the flexible tube 26, as shown in FIG. 7. That is, the structure for fixing the first connection mouth ring 70 to the distal end of the flexible tube 26 in this embodiment is the same as the structure for fixing the second connection mouth ring 100 to the proximal end of the flexible tube 26 described in the first embodiment.

The first connection mouth ring 70 fixed to the distal end of the flexible tube 26 includes an inner mouth ring 132 and an outer mouth ring 134.

The inner mouth ring 132 includes a cylindrical portion 132a disposed inside the helical tube 62, and an outward flange portion 132b disposed at the distal end of the cylindrical portion 132a. The cylindrical portion 132a and the outward flange portion 132b have the same inside diameter and are flush with each other. The outward flange portion 132b projects diametrically outwardly with respect to the outer peripheral surface of the cylindrical portion 132a. Thus, a step portion (collision portion) 132c is formed between the cylindrical portion 132a and the flange portion 132b. The distal ends of the helical tube 62, a braid tube 64 and an outer tube 66, that is, the distal end of the flexible tube 26 are positioned by the step portion 132c between the cylindrical portion 132a and the flange portion 132b.

The outside diameter of the inner mouth ring 132 is formed to be larger than the inside diameter of the distal end of the helical tube 62 so that the inner peripheral surface of the helical tube 62 may be in close contact with the outer peripheral surface of the inner mouth ring 132 when the helical tube 62 is placed in a natural state. The helical tube 62 is fixed to the inner mouth ring 132 by being laser-welded from the outside of the helical tube 62. That is, welded portions (helical tube displacement preventing portions) W (see FIG. 4) are formed. Thus, when the outer mouth ring 134 is caulked, the helical tube 62 is prevented from being moved (displaced) with respect to the inner mouth ring 132. Consequently, the helical tube 62 is tightened up, such that the inside diameter of the cylindrical portion 132a of the inner mouth ring 132 is prevented from being reduced.

The outer mouth ring 134 includes a cylindrical portion 134a disposed outside the flexible tube 26, and an inward flange portion 134b disposed at the distal end of the cylindrical portion 134a. The cylindrical portion 134a and the inward flange portion 134b have the same outside diameter and are flush with each other. Further, the inward flange portion 134b projects diametrically inwardly with respect to the outer peripheral surface of the cylindrical portion 134a. Thus, a step portion (collision portion) 134c is formed between the cylindrical portion 134a and the flange portion 134b.

Furthermore, on the distal side of the flange portion 134b of the outer mouth ring 134, an opening 72 is formed where a connecting pin 52b for engaging the bending tube 52 of the bending portion 24 is disposed. Thus, the connecting pin 52b is disposed in the distal opening 72 such that the outer mouth ring 134 is linked to the bending tube 52.

The outside diameter of the outward flange portion 132b of the inner mouth ring 132 is smaller than the inside diameter of the cylindrical portion 134a of the outer mouth ring 134, and larger than the inside diameter of the inward flange portion 134b of the outer mouth ring 134. Moreover, the distal end of the inner mouth ring 132 is positioned by the step portion 134c between the cylindrical portion 134a and the flange portion 134b.

The cylindrical portion 134a of the outer mouth ring 134 has such an inside diameter that not only the inner mouth ring 132 but also the helical tube 62, the braid tube 64 and the outer tube 66 are disposed therein.

It is to be noted that the structure of a second connection mouth ring 100 is the same as the structure described in the first embodiment and is therefore not described.

As described above, the following can be said according to this embodiment.

The structure of the second connection mouth ring 100 for connecting the flexible tube 26 and the operation portion 14 in the first embodiment can be similarly used for the first connection mouth ring 70 for connecting the bending portion 24 and the flexible tube 26.

Moreover, in the description of this embodiment, the first connection mouth ring 70 for connecting to the bending tube 52 is disposed at the distal end of the flexible tube 26, and the second connection mouth ring 100 for linking to the operation portion 14 is disposed at the proximal end of the flexible tube 26. However, it is also suitable to use the above-described structure of the first connection mouth ring 70 and the second connection mouth ring 100 as the structure of a connection mouth ring at the end of the flexible tube (corrugated tube) 42 of the universal cable 16. That is, it is also suitable to provide a connection mouth ring having the same structure as the second connection mouth ring 100 for connecting to the operation portion 14, at the end of the flexible tube 42 of the universal cable 16.

Although not described below in the third to twelfth embodiments, connection mouth rings having the same structure can be used for the second connection mouth ring 100 for connecting to the operation portion 14, the first connection mouth ring 70 for linking to the bending portion 24, and the universal cable 16, as in this embodiment. Needless to say, it is also suitable to properly combine and use the structures described in the respective embodiments.

In addition, while the medical endoscope 10 having the insertion portion 12 and the universal cable 16 has been shown in FIG. 1, etc. and described in the above first and second embodiments, the present invention may also be used for the end of a flexible member (a flexible tube or corrugated tube) of, for example, as insertion portions of various endoscopes such as an industrial endoscope (not shown).

Third Embodiment

Next, a third embodiment is described with reference to FIG. 8.

As shown in FIG. 8, a convex-concave portion 142 having a convex portion (crest portions) 142a and a concave portion (root portions) 142b is formed in the inner peripheral surface of the cylindrical portion 104a of the outer mouth ring 104 of the second connection mouth ring 100 in this embodiment. When the cylindrical portion 104a of the outer mouth ring 104 is caulked inward, the convex portion 142a in the inner peripheral surface of the cylindrical portion 104a of the outer mouth ring 104 cuts into the outer tube 66, so that greater fixing strength can be obtained when the second connection mouth ring 100 is fixed to the proximal end of the flexible tube 26.

Further, the convex-concave portion 142 may be formed as a female screw thread, for example. Moreover, if the convex portion 142a is formed on the inside of the cylindrical portion 104a of the outer mouth ring 104, various shape are permitted, such as a rough grain-finished shape.

Fourth Embodiment

Next, a fourth embodiment is described with reference to FIG. 9.

The inside diameters of the cylindrical portion 102a and the outward flange portion 102b of the inner mouth ring 102 are formed to be equal to or larger than the minimum diameter of the flexible tube 26, that is, the minimum diameter of the helical tube 62. Thus, the inner peripheral surface of the helical tube 62 comes into close contact with the outer peripheral surface of the cylindrical portion 102a of the inner mouth ring 102 owing to the elastic force of the helical tube 62. Consequently, stable welding can be carried out when the helical tube 62 is fixed to the inner mouth ring 102 by welding. That is, welded portions (helical tube displacement preventing portions) W can be easily formed.

Furthermore, the inside diameters of the cylindrical portion 102a and the outward flange portion 102b of the inner mouth ring 102 are formed to be equal to or larger than the minimum diameter of the flexible tube 26, that is, the minimum diameter of the helical tube 62. Thus, if a core bar (not shown) is disposed, it is possible to eliminate the problem of a local decrease of the inside diameter of a second connection mouth ring 100 with respect to the inside diameter of the flexible tube 26 as shown in FIG. 9 when the second connection mouth ring 100 is caulked on the flexible tube 26. That is, as shown in FIG. 9, the inside diameter of the inner mouth ring 102 of the second connection mouth ring 100 is made equal to or larger than the minimum diameter of the helical tube 62 of the flexible tube 26, such that it is possible to prevent the problem of difficulty in inserting various built-in objects such as an unshown illumination optical system and observation optical system.

Fifth Embodiment

Next, a fifth embodiment is described with reference to FIG. 10.

As shown in FIG. 10, the outer peripheral surface of the proximal end of the outer tube 66 of the flexible tube 26 is formed into a small thickness by, for example, polishing or removal processing. In general, the outer tube 66 has greater variations in size (thickness) than other members such as the helical tube 62 and the braid tube 64, but any variations in the size of the outer tube 66 can be eliminated by, for example, polishing. The variations in the dimension of the outside diameter of the outer tube 66 are inhibited in this manner, such that variations in the strength of the connection of a second connection mouth ring 100 to the proximal end of the flexible tube 26 can be eliminated. As a result, the quality of a unit in which the second connection mouth ring 100 is fixed to the flexible tube 26 can be substantially uniform.

Sixth Embodiment

Next, a sixth embodiment is described with reference to FIG. 11.

Figure 11:
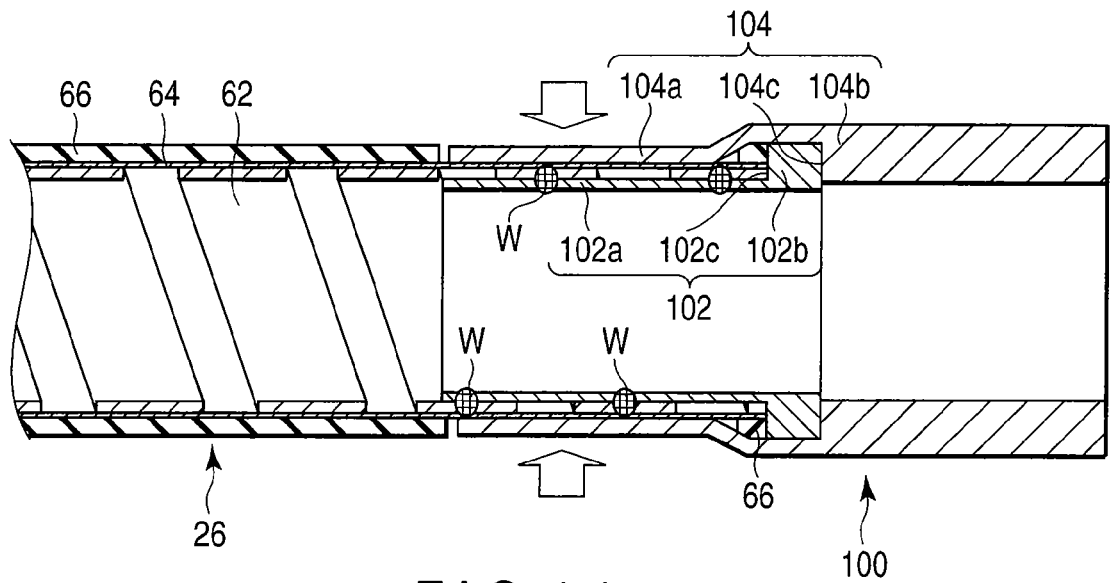
FIG. 11 is a schematic longitudinal sectional view showing how the operation portion connection mouth ring is fixed to the proximal end of the flexible tube of the insertion portion of the endoscope according to the sixth embodiment.

As shown in FIG. 11, the outer tube 66 is removed in a part where the cylindrical portion 104a of the outer mouth ring 104 is caulked. Thus, when the cylindrical portion 104a of the outer mouth ring 104 is caulked from the outside of the proximal end of the flexible tube 26, the cylindrical portion 104a of the outer mouth ring 104 is not caulked on the outer tube 66 having greater variations in dimension (thickness) than other members such as the helical tube 62 and the braid tube 64, such that the dimensional variations can be reduced at the position where the cylindrical portion 104a of the outer mouth ring 104 is caulked. That is, the quality of a unit in which the second connection mouth ring 100 is fixed to the flexible tube 26 can be substantially uniform.

In addition, it is acceptable to leave the proximal end of the outer tube 66 unremoved to prevent the proximal end of the braid tube 64 from being broken up.

Seventh Embodiment

Next, a seventh embodiment is described with reference to FIG. 12. This embodiment is a modification of the sixth embodiment.

Figure 12:
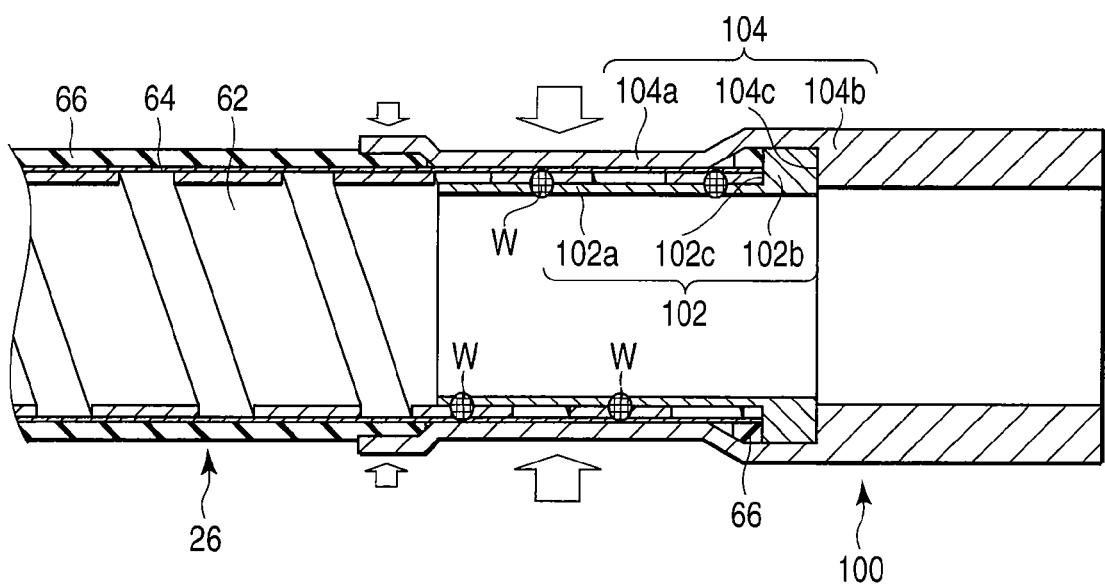
FIG. 12 is a schematic longitudinal sectional view showing how the operation portion connection mouth ring is fixed to the proximal end of the flexible tube of the insertion portion of the endoscope according to the seventh embodiment.

As shown in FIG. 12, part of the outer tube 66 is also caulked by the cylindrical portion 104a of the outer mouth ring 104, in contrast with the sixth embodiment shown in FIG. 11. Thus, airtightness between the outer mouth ring 104 of the second connection mouth ring 100 and the outer tube 66 can be assured.

Eighth Embodiment

Figure 13:
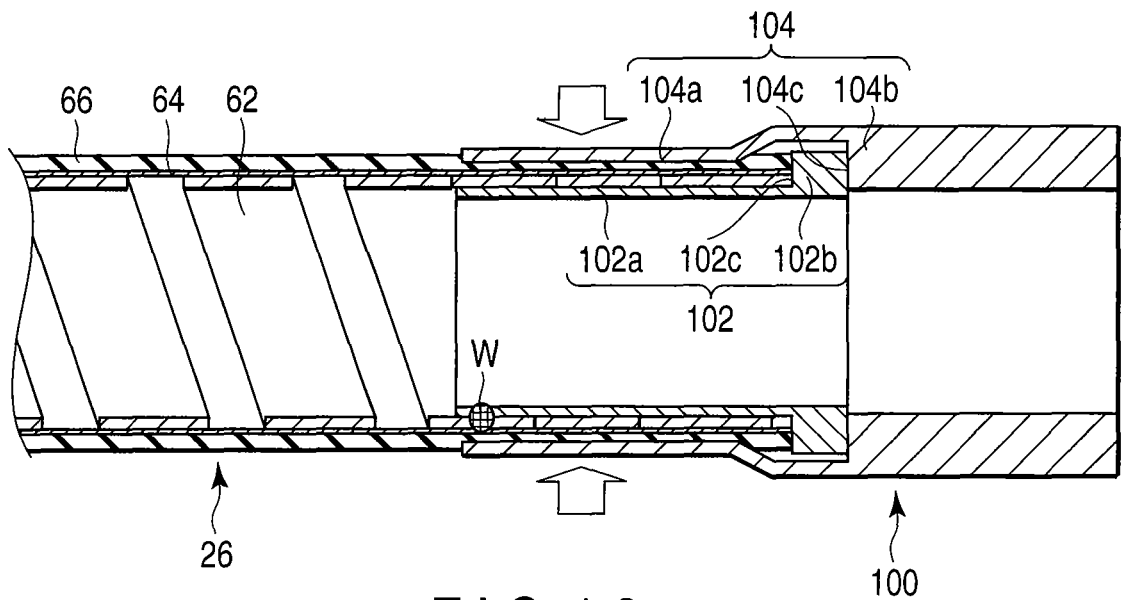
FIG. 13 is a schematic longitudinal sectional view showing how the operation portion connection mouth ring is fixed to the proximal end of the flexible tube of the insertion portion of the endoscope according to the eighth embodiment.

Next, an eighth embodiment is described with reference to FIG. 13.

The helical tube 62 is elastic. Thus, the distance (pitch) between the edges of the strip plate of the helical tube 62 can be easily changed by applying a load. As shown in FIG. 13, here, the edges of the strip plate at the proximal end of the helical tube 62 are placed in collision with each other so that the proximal end of the helical tube 62 is in collision with the step portion 102c of the inner mouth ring 102. Then, the side of the flexible tube 26 proximate to its distal end is laser-welded to the cylindrical portion 102a of the inner mouth ring 102 such that the inner mouth ring 102 is fixed to the flexible tube 26.

The helical tube 62 is prevented from moving between the proximal end of the helical tube 62 placed in collision with the step portion 102c of the inner mouth ring 102 and welded portions W laser-welded to the cylindrical portion 102a of the inner mouth ring 102. Therefore, when the cylindrical portion 104a of the outer mouth ring 104 is caulked by, for example, the welded portion W at one place, tightening of the helical tube 62 can be prevented.

Ninth Embodiment

Next, a ninth embodiment is described with reference to FIG. 14 to FIG. 15C. This embodiment is a modification of the eighth embodiment.

Figure 14:
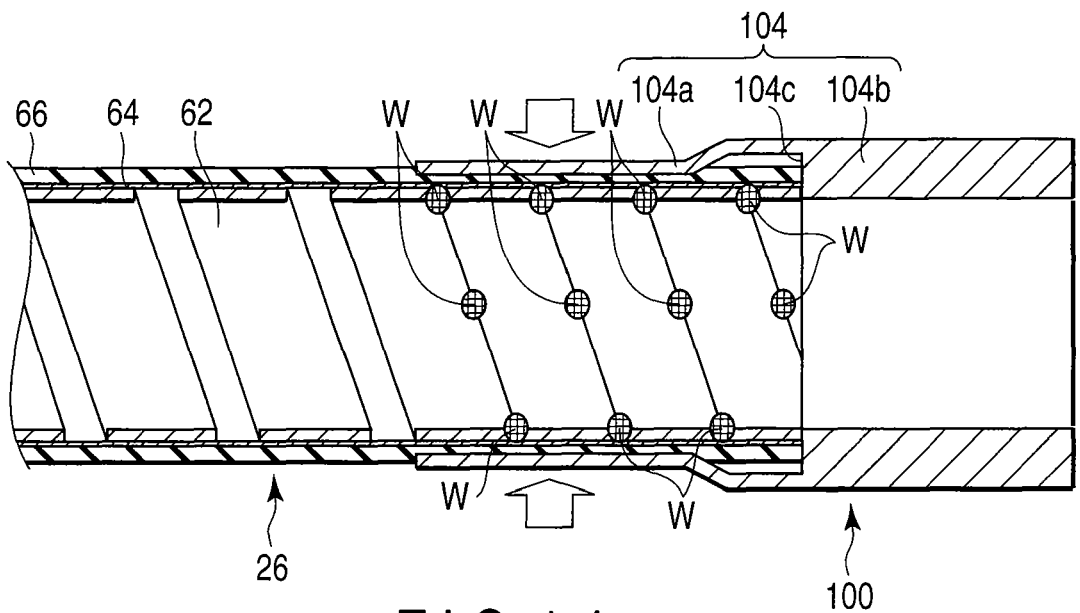
FIG. 14 is a schematic longitudinal sectional view showing how the operation portion connection mouth ring is fixed to the proximal end of the flexible tube of the insertion portion of the endoscope according to the ninth embodiment.

As shown in FIG. 14, since the helical tube 62 is elastic, the edges of the strip plate of the helical tube 62 are formed in collision with each other at the proximal end of the helical tube 62. Further, in the part where the edges of the strip plate of the helical tube 62 are in collision with each other at the proximal end of the helical tube 62, a plurality of points are joined by laser welding. Laser-welded portions W prevent the movement (displacement) of the adjacent parts of the strip plate of the helical tube 62. Moreover, the proximal end of the helical tube 62 is in collision with the step portion 104c of the outer mouth ring 104. Since the proximal end of the helical tube 62 is thus in collision with the step portion (collision portion) 104c of the outer mouth ring 104, the helical tube 62 can be axially positioned with respect to the outer mouth ring 104 of the second connection mouth ring 100.

At this point, even if the helical tube 62 is not fixed to the inner mouth ring 102, that is, even if the inner mouth ring 102 is not disposed, the axial movement (displacement) of the helical tube 62 can be prevented by the step portion 104c of the outer mouth ring 104, and tightening of the helical tube 62 can be prevented by the welded portions W, such that deformation due to the caulking of the cylindrical portion 104a of the outer mouth ring 104 can be accommodated by the helical tube 62. That is, in this embodiment, the second connection mouth ring 100 does not need the inner mouth ring 102.

In addition, while the welded portions W are arranged at proper intervals in FIG. 14 to FIG. 15C, it is also suitable for the welded portions to be continuous (a circumferentially formed welded portion).

Here, a method of attaching the second connection mouth ring 100 to the proximal end of the flexible tube 26 is illustrated.

First, as shown in FIG. 6A described in the first embodiment, the proximal ends of the helical tube 62, the braid tube 64 and the outer tube 66 are cut. At this point, the proximal ends of the helical tube 62, the braid tube 64 and the outer tube 66 are cut at about 90 degrees to their axial direction. Burrs in the proximal ends of the helical tube 62, the braid tube 64 and the outer tube 66 are removed so that the proximal end surface of the flexible tube 26 may be even.

Then, as shown in FIG. 6B, of the helical tube 62, the braid tube 64 and the outer tube 66, the helical tube 62 is drawn to the proximal side with respect to the braid tube 64 and the outer tube 66.

As shown in FIG. 15A, a welding core bar CR is put into the proximal end of the helical tube 62, and the edges of the strip plate at the proximal end of the helical tube 62 are placed into collision with each other so that the strip plate may be dense. In this state, the edges of the strip plate at the proximal end of the helical tube 62 are welded by laser. The welding core bar CR is removed from the proximal end of the helical tube 62.

As shown in FIG. 15B, the helical tube 62 is pressed into the braid tube 64 and the outer tube 66, and the outer mouth ring 104 is disposed at the proximal end of the flexible tube 26.

As shown in FIG. 15C, the caulking core bar C is put into the proximal side of the helical tube 62, such that the cylindrical portion 104a of the outer mouth ring 104 is caulked.

Tenth Embodiment

Next, a tenth embodiment is described with reference to FIG. 16.

Figure 16:
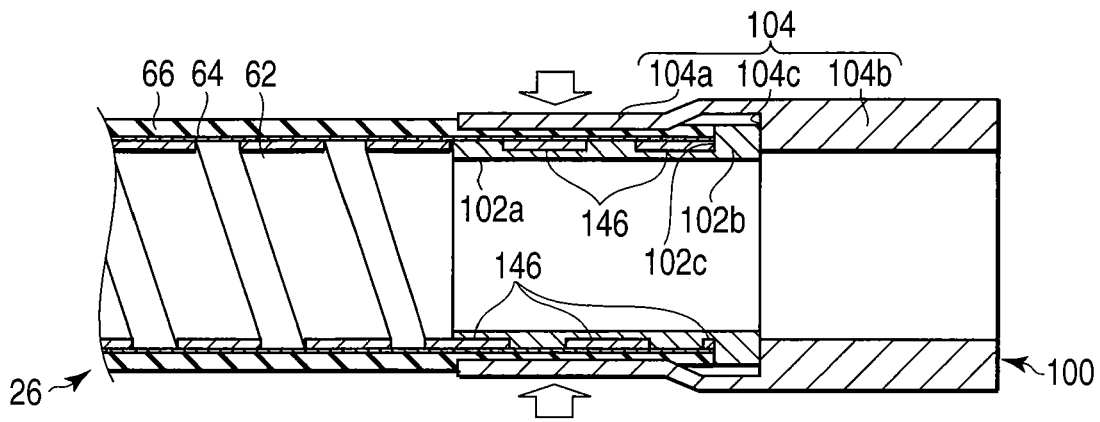
FIG. 16 is a schematic longitudinal sectional view showing how the operation portion connection mouth ring is fixed to the proximal end of the flexible tube of the insertion portion of the endoscope according to the tenth embodiment.

As shown in FIG. 16, a groove portion 146 adapted to the width of the strip plate of the helical tube 62 is helically formed in the outer peripheral surface of the cylindrical portion 102a of the inner mouth ring 102. Thus, the proximal end of the helical tube 62 moves and fits into the groove portion 146, and when the proximal end of the helical tube 62 is in collision with the step portion 102c of the inner mouth ring 102, the helical tube 62 does not move (displace). That is, even if the cylindrical portion 104a of the outer mouth ring 104 is caulked from the outside of the flexible tube 26, tightening of the helical tube 62 is prevented. Further, owing to the friction between the braid tube 64 and the outer tube 66, the helical tube 62 is prevented from moving in the helical direction of its strip plate. Consequently, the second connection mouth ring 100 can be fixed to the proximal end of the flexible tube 26 with no troublesome tasks such as laser welding.

Eleventh Embodiment

Next, an eleventh embodiment is described with reference to FIG. 17. This embodiment is a modification of the tenth embodiment.

Figure 17:
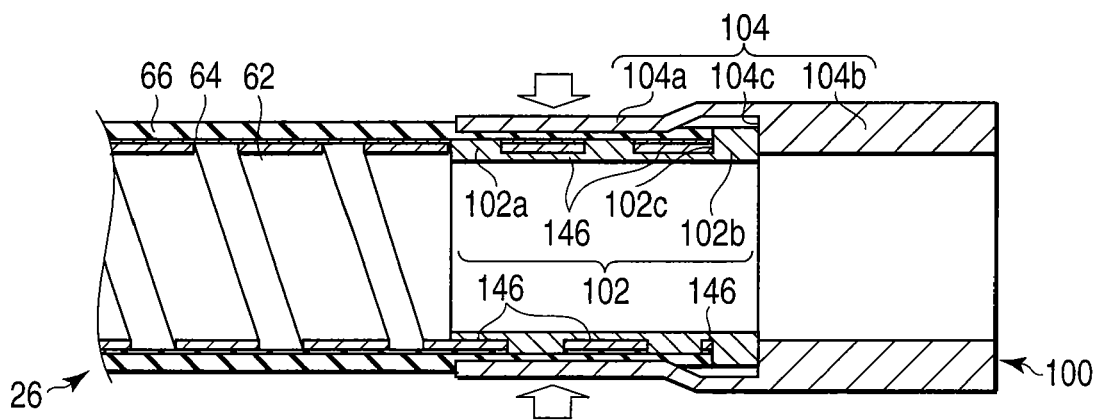
FIG. 17 is a schematic longitudinal sectional view showing how the operation portion connection mouth ring is fixed to the proximal end of the flexible tube of the insertion portion of the endoscope according to the eleventh embodiment.

As shown in FIG. 17, in the example of this embodiment, the depth of the groove portion 146 shown in FIG. 16 described in the tenth embodiment is larger than the thickness of the strip plate of the helical tube 62. In such a structure, the caulking of the cylindrical portion 104a of the outer mouth ring 104 is received by the outermost peripheral surface of the cylindrical portion 102a of the inner mouth ring 102. Thus, the caulking of the cylindrical portion 104a of the outer mouth ring 104 is prevented from directly affecting the helical tube 62, such that tightening of the helical tube 62 is not easily caused, and stronger caulking can be achieved. Consequently, greater fixing strength can be obtained between the flexible tube 26 and the second connection mouth ring 100.

Twelfth Embodiment

Next, a twelfth embodiment is described with reference to FIG. 18.

Figure 18:
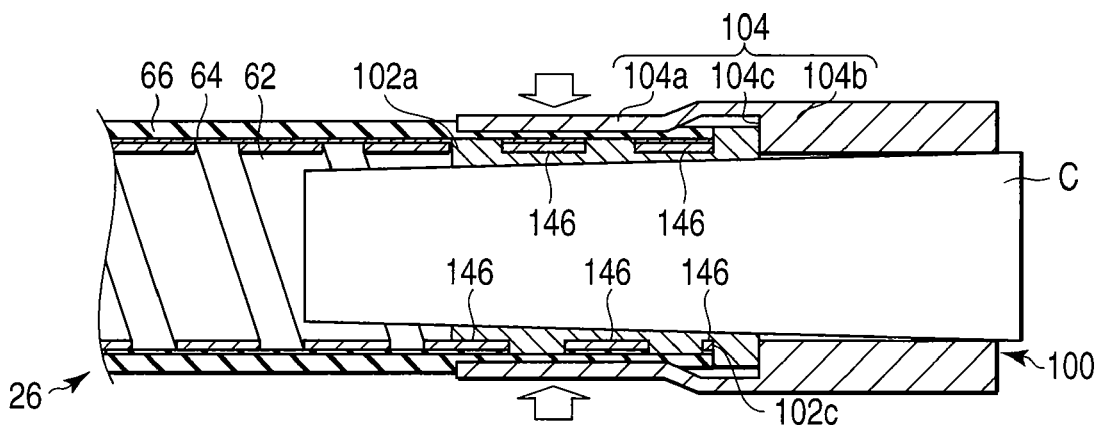
FIG. 18 is a schematic longitudinal sectional view showing how the operation portion connection mouth ring is fixed to the proximal end of the flexible tube of the insertion portion of the endoscope according to the twelfth embodiment.

As shown in FIG. 18, the inner peripheral surfaces of the cylindrical portion 102a and the flange portion 102b of the inner mouth ring 102 are tapered so that the inside diameter increases toward their proximal side. The caulking core bar C used is formed accordingly to adapt to the taper angle.

Thus, when the core bar C is removed, the inner peripheral surfaces of the cylindrical portion 102a and the flange portion 102b of the inner mouth ring 102 function as removal slopes, so that the core bar C can be easily removed. Moreover, since the core bar C can thus be easily removed, the cylindrical portion 104a of the outer mouth ring 104 can be more strongly caulked. Consequently, greater fixing strength can be obtained between the flexible tube 26 and the second connection mouth ring 100.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising: a flexible tube having a helical tube in which a thin strip plate is helically wound, a braid tube covering an outside of the helical tube, and a flexible outer tube covering an outside of the braid tube;
   a connection mouth ring plastically deformed and fixed to an end of the flexible tube;
   and a helical tube displacement preventing portion which is configured to prevent displacement of the strip plate of the helical tube at the end of the flexible tube to which the connection mouth ring is fixed, when the connection mouth ring is fixed to the end of the flexible tube, wherein at the end of the flexible tube to which the connection mouth ring is fixed, the helical tube displacement preventing portion places axially adjacent edges of the strip plate of the helical tube in close contact with each other, and places an end of the helical tube in collision with the connection mouth ring, wherein the connection mouth ring includes an inner mouth ring disposed inside the end of the flexible tube, and an outer mouth ring disposed outside the end of the flexible tube, and the helical tube displacement preventing portion fixes the helical tube to the outside of the inner mouth ring to prevent the displacement of the helical tube.

2. The endoscope according to claim 1, wherein the helical tube displacement preventing portion includes, in the inner mouth ring, a collision portion with which the end of the helical tube is brought into collision.

3. The endoscope according to claim 1, wherein the helical tube displacement preventing portion includes, on the outer periphery of the inner mouth ring, a groove portion into which the strip plate of the helical tube is fitted.

* * * * *